US012759196B2

(12) United States Patent
Kang et al.

(10) Patent No.: US 12,759,196 B2
(45) Date of Patent: Oct. 13, 2026

(54) SOLID MICRONEEDLE COMPRISING DRUG AND METHOD FOR MANUFACTURING THE SAME

(71) Applicant: LG HOUSEHOLD & HEALTH CARE LTD., Seoul (KR)

(72) Inventors: Seong-Su Kang, Seoul (KR); Seung-Hyun Jun, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 700 days.

(21) Appl. No.: 18/176,606

(22) Filed: Mar. 1, 2023

(65) Prior Publication Data

US 2023/0278265 A1 Sep. 7, 2023

(30) Foreign Application Priority Data

Mar. 3, 2022 (KR) ........................ 10-2022-0027549

(51) Int. Cl.

| | |
|---|---|
| ***A61M 37/00*** | (2006.01) |
| ***A61K 9/00*** | (2006.01) |
| ***B29C 39/02*** | (2006.01) |
| *B29K 67/00* | (2006.01) |
| *B29L 31/00* | (2006.01) |

(52) U.S. Cl.

CPC .......... *B29C 39/026* (2013.01); *A61K 9/0021* (2013.01); *B29K 2067/046* (2013.01); *B29L 2031/7544* (2013.01)

(58) Field of Classification Search

CPC ...... A61M 37/0015; A61M 2037/0023; A61M 2037/0046; A61M 2037/0053

See application file for complete search history.

(56) References Cited

U.S. PATENT DOCUMENTS

2008/0269685 A1* 10/2008 Singh ..................... A61K 38/29 604/173
2016/0374939 A1* 12/2016 Shastry ................ A61K 9/0021 264/496

FOREIGN PATENT DOCUMENTS

| | | | |
|---|---|---|---|
| CN | 109364366 | A | 2/2019 |
| KR | 10-2015-0085502 | A | 7/2015 |
| WO | 2014/015165 | A1 | 1/2014 |

OTHER PUBLICATIONS

Li et al., "Rapidly separable microneedle patch for the sustained release of a contraceptive", Nature Biomedical Engineering, 12 pages, 2019.
Yavuz et al., "Silk Fibroin Microneedle Patches for the Sustained Release of Levonorgestrel", ACS Appl. Bio Mater., 2020, vol. 3, pp. 5375-5382.

* cited by examiner

*Primary Examiner* — Deanna K Hall
(74) *Attorney, Agent, or Firm* — Vorys, Sater, Seymour and Pease LLP; Mih Suhn Koh

(57) ABSTRACT

The present disclosure relates to a solid microneedle structure prepared using a water-insoluble polymer and a technique for manufacturing the same, wherein the technique can control the drug release rate of the microneedle: a rapid-release type or a sustained release type, the drug included in the microneedle may be various cosmetic or pharmaceutical active ingredients, and the microneedle can have an appropriate release rate suitable for the drug by the method of the invention.

11 Claims, 10 Drawing Sheets

【FIG. 1】
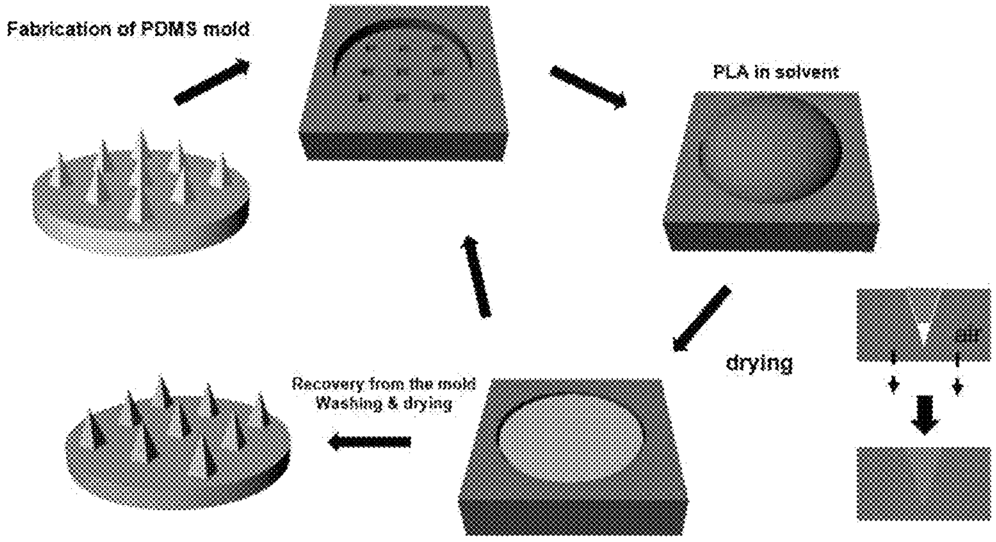
【FIG. 2】
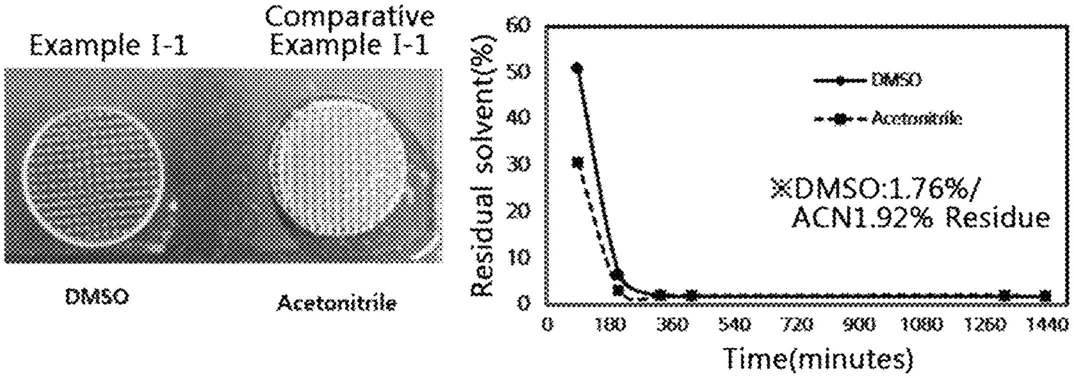

【FIG. 3】
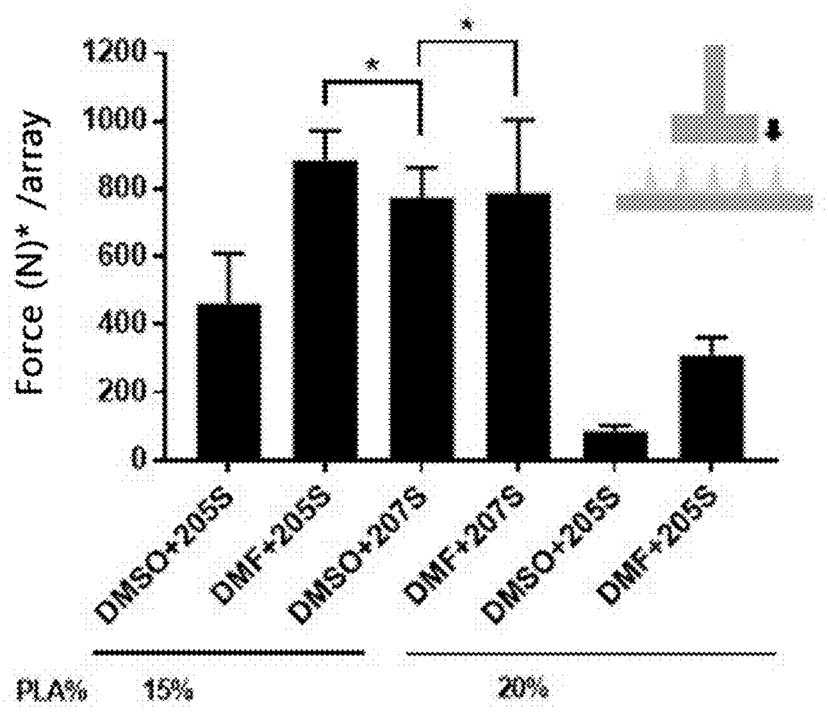
*Force measured at a strain of 300 μm
【FIG. 4】
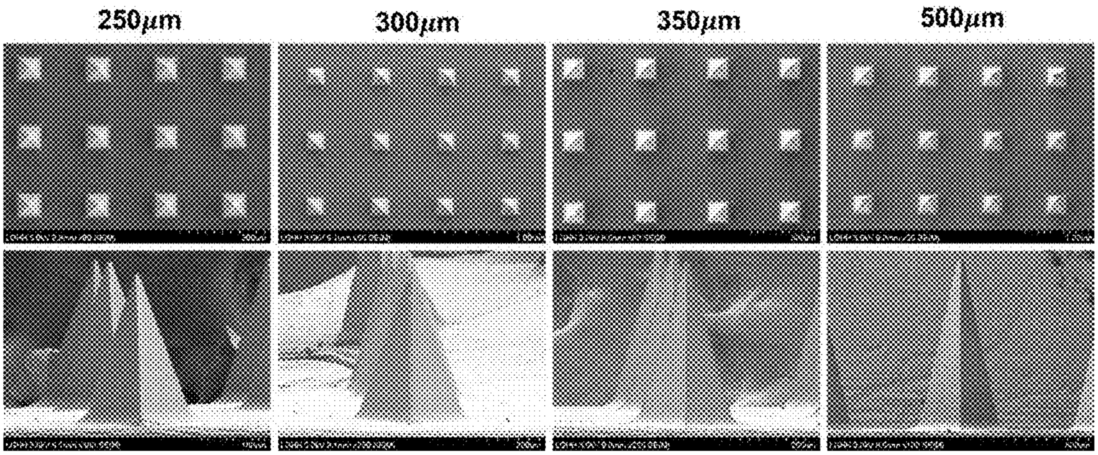

【FIG. 5】
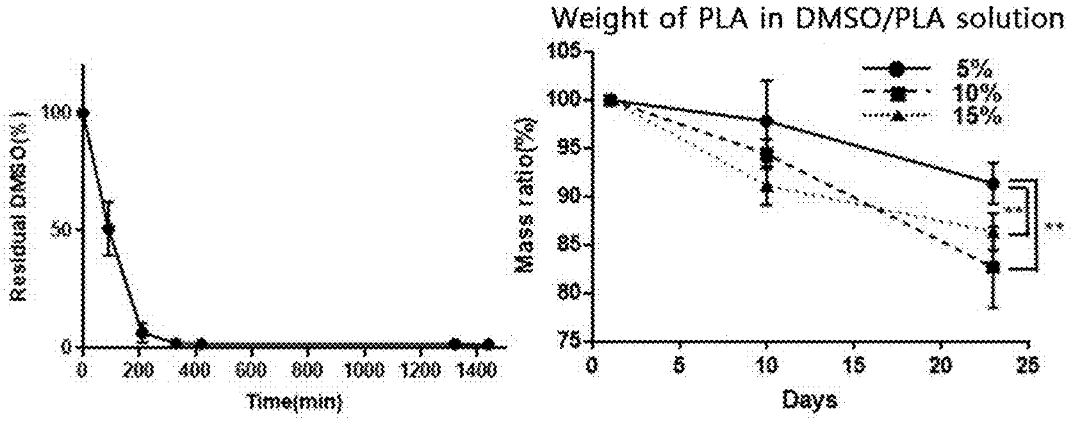
【FIG. 6】
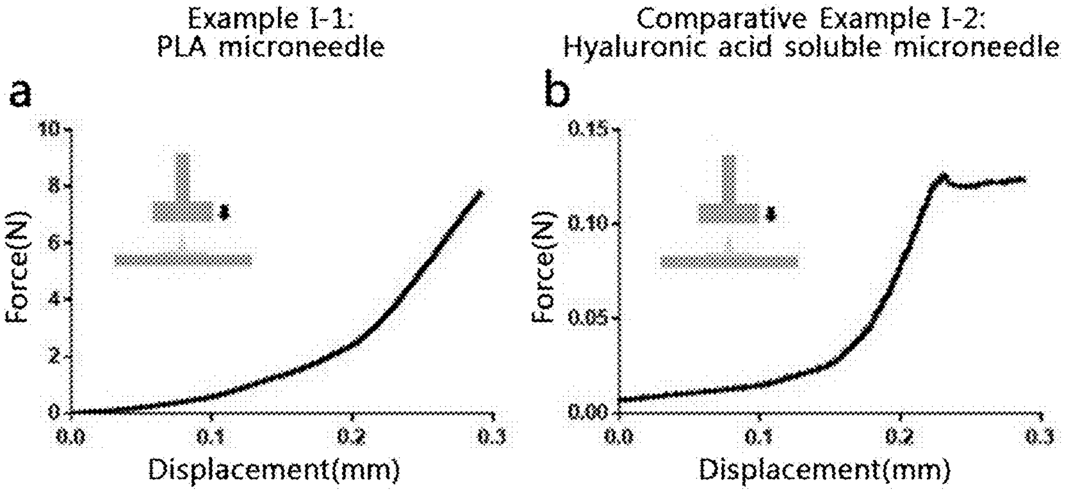

【FIG. 7】
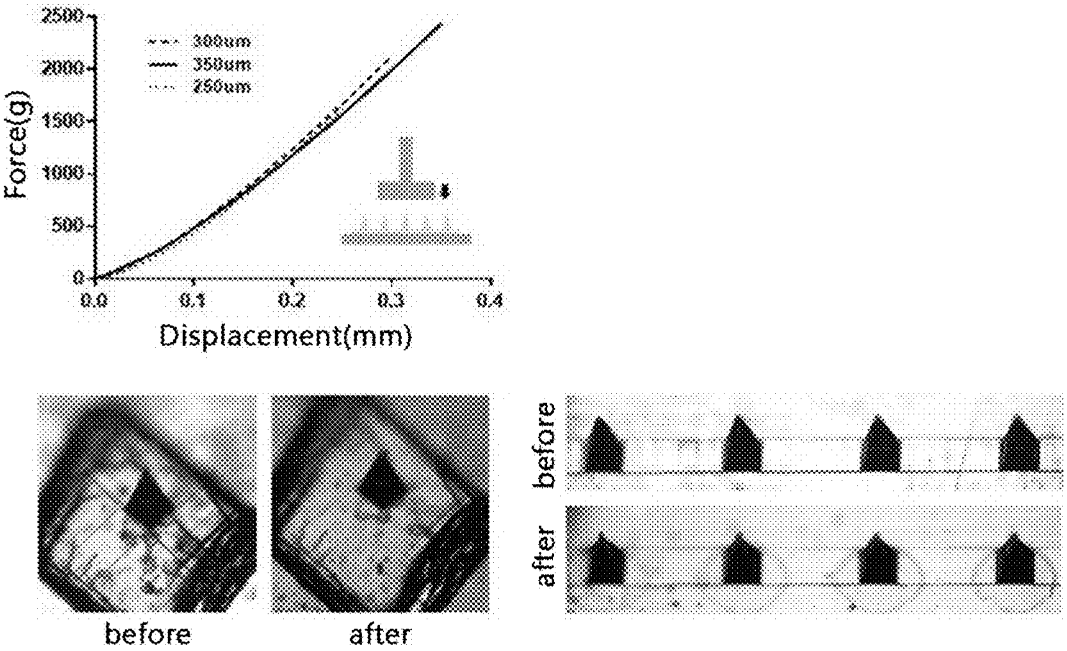

【FIG. 8A】
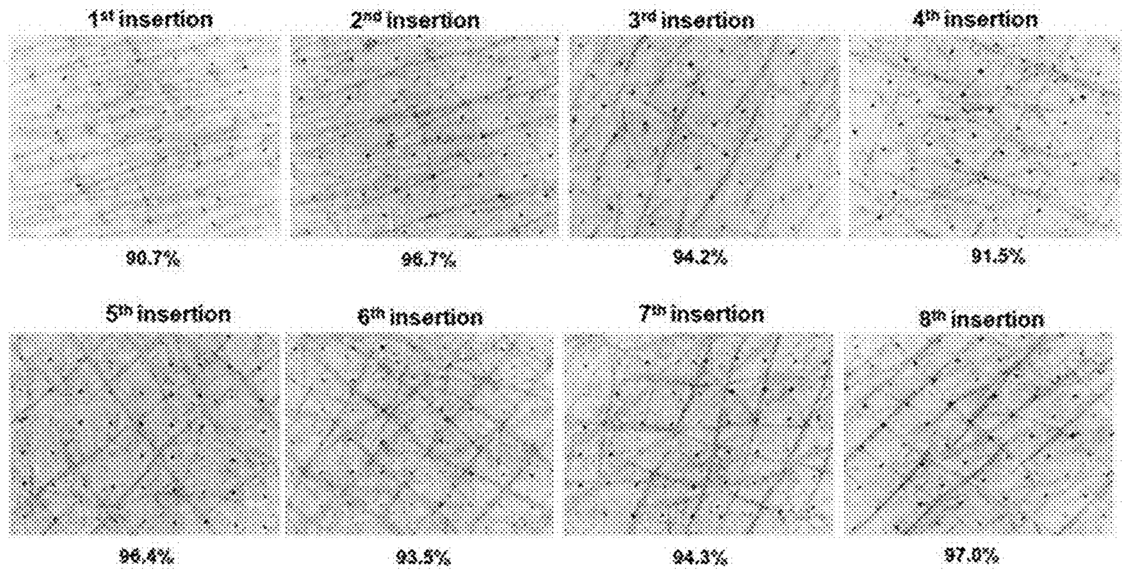
【FIG. 8B】
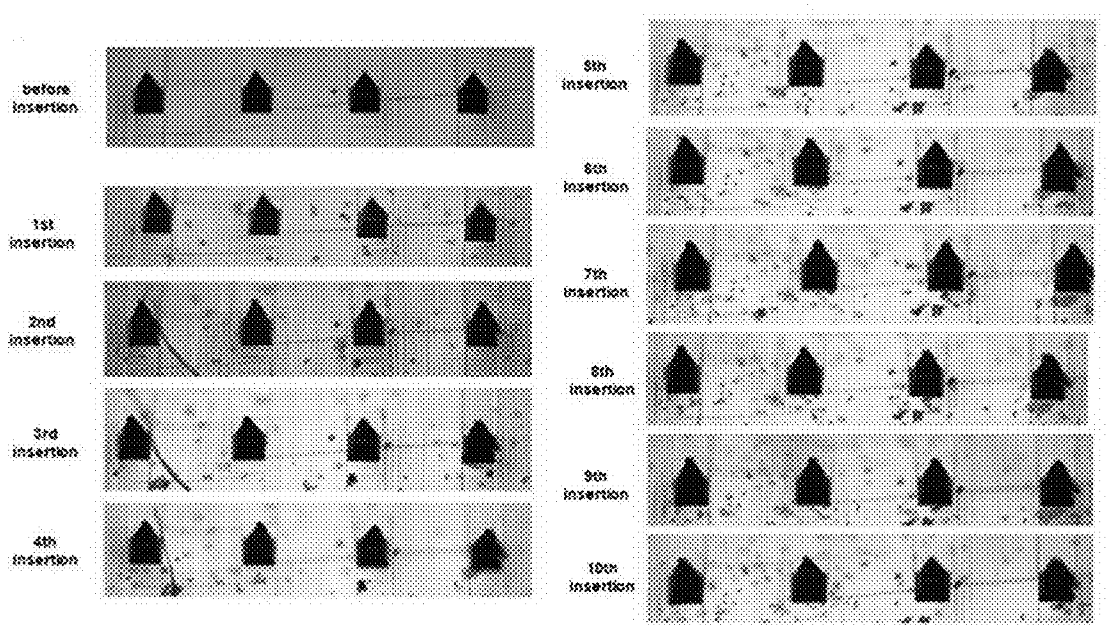

【FIG. 9】
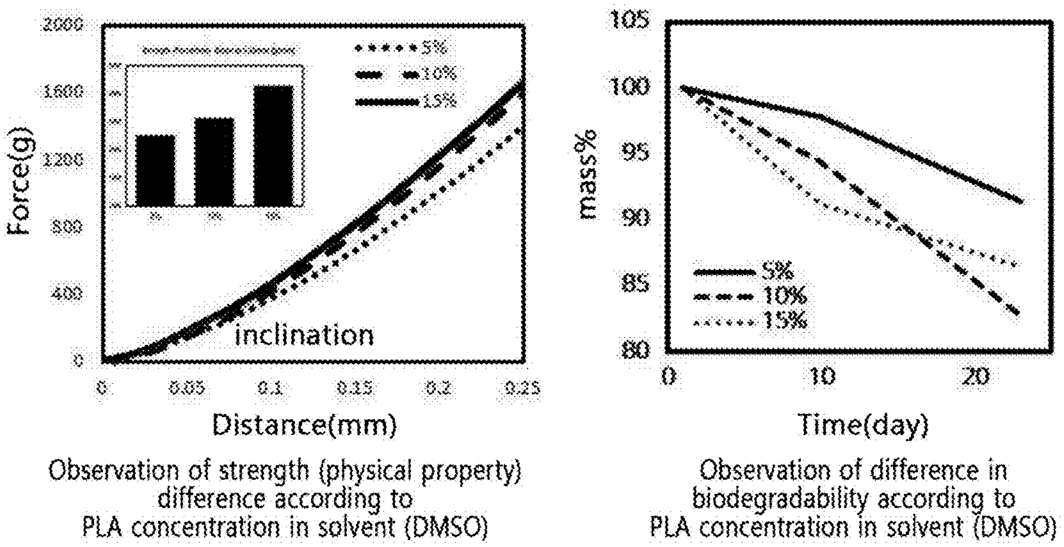
【FIG. 10】
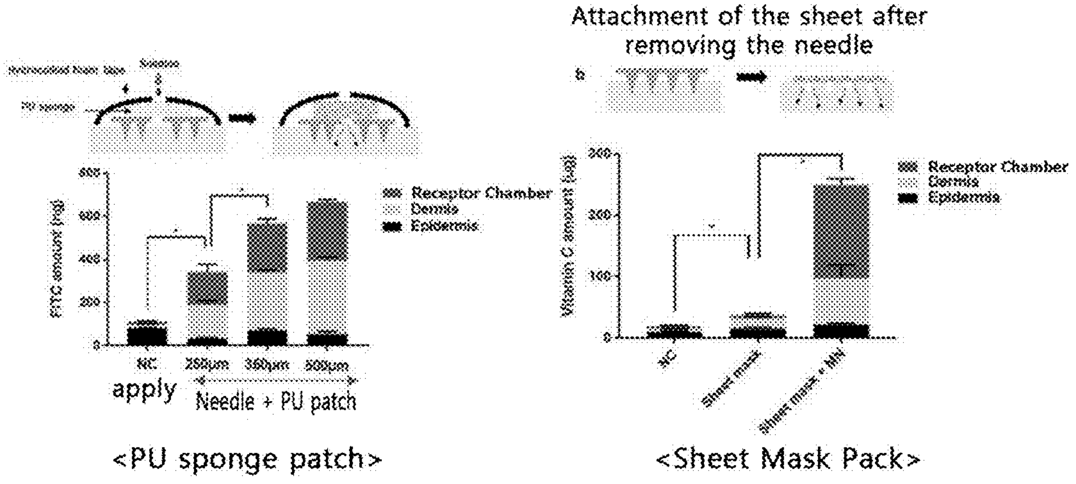

【FIG. 11】
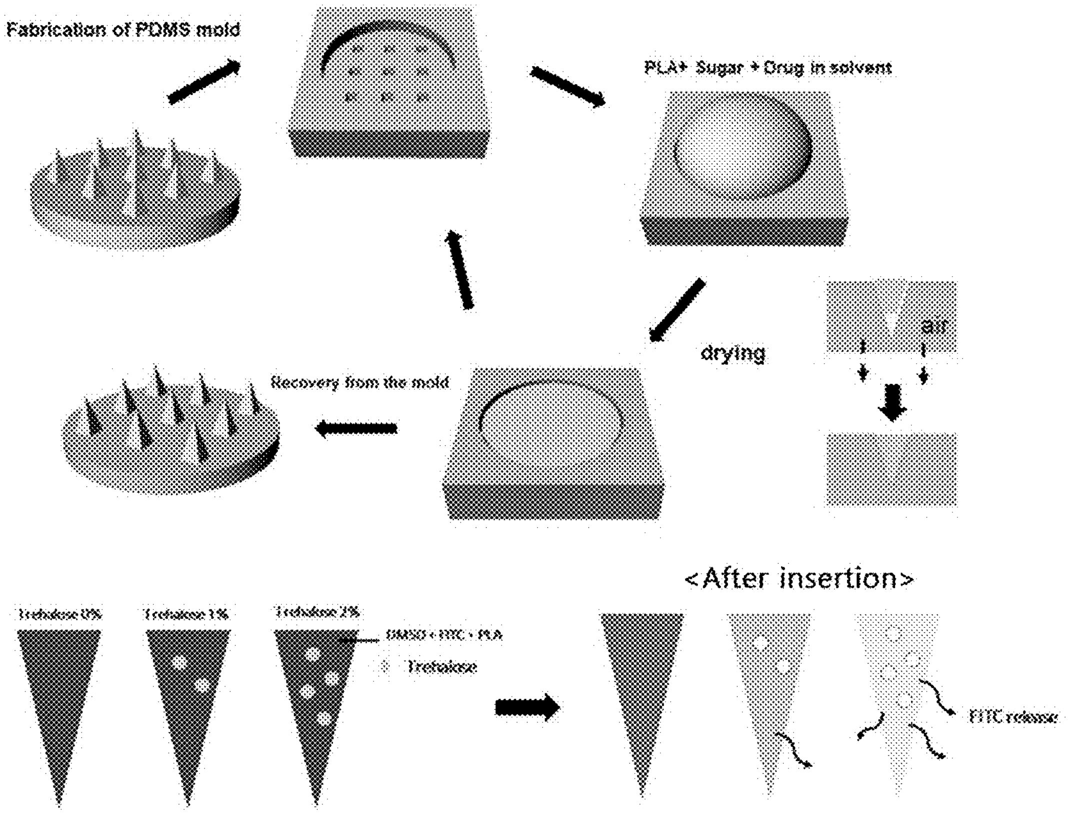

【FIG. 12】
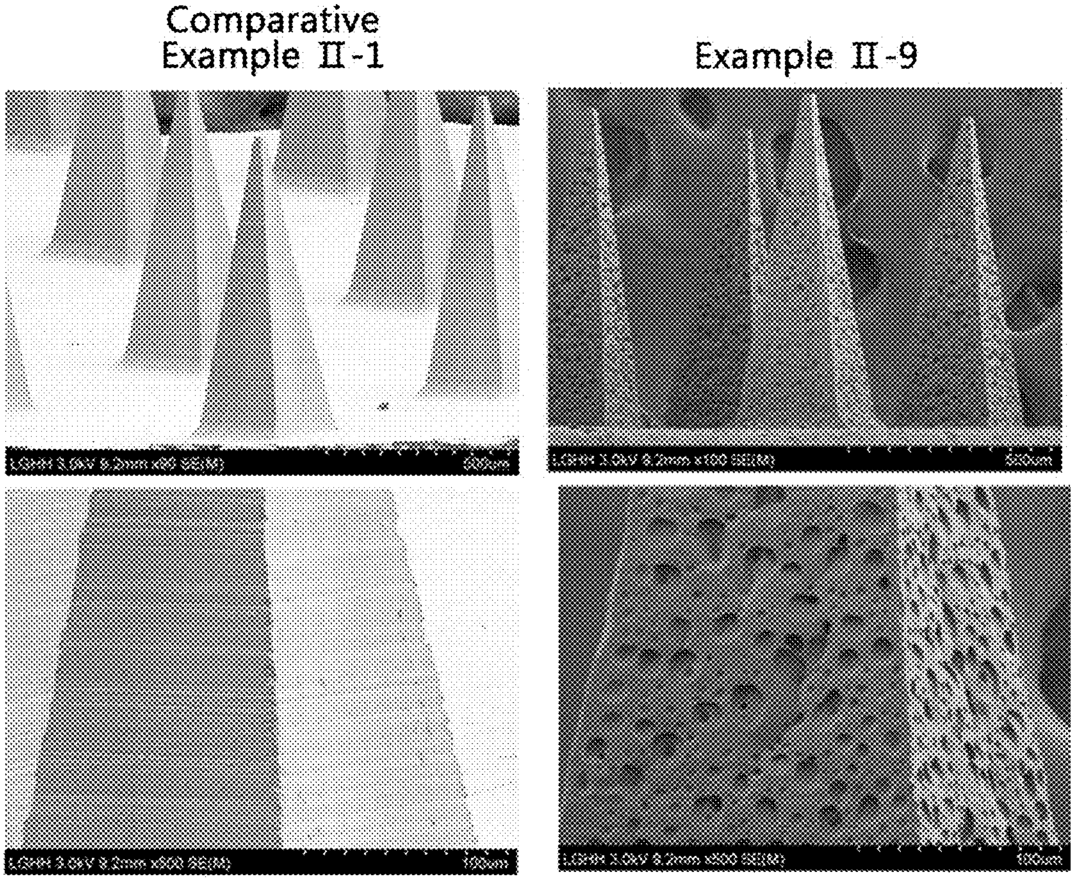
【FIG. 13】
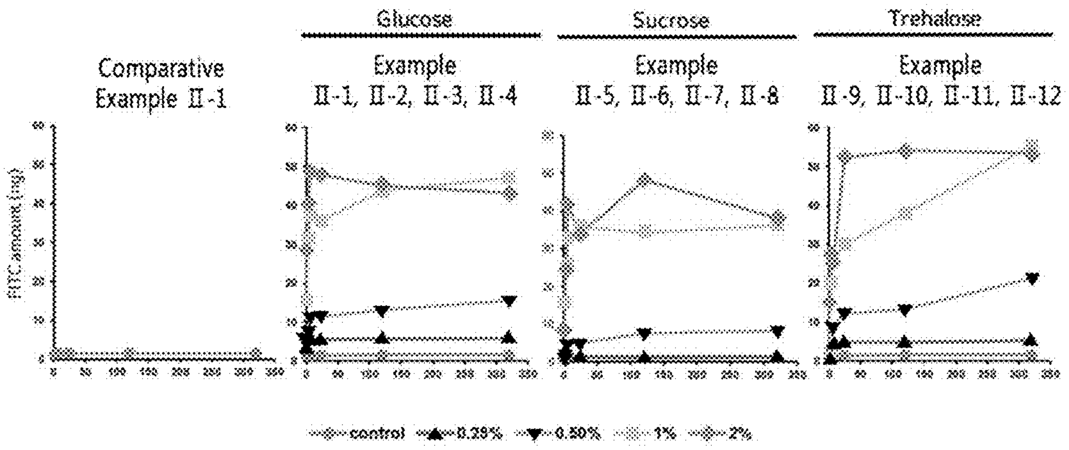

【FIG. 14】
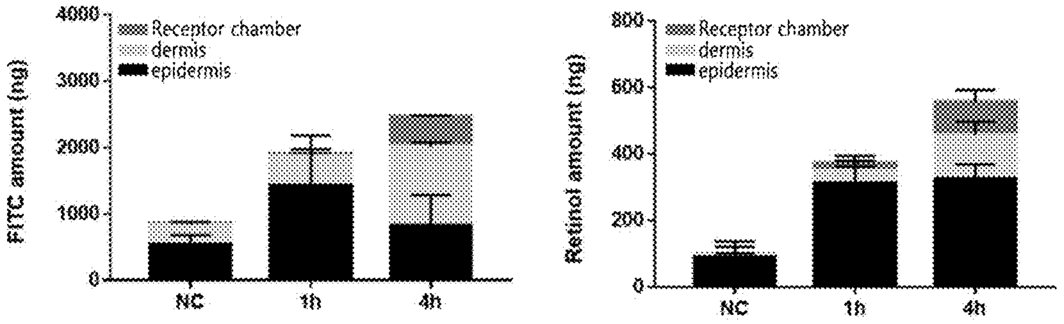
【FIG. 15】
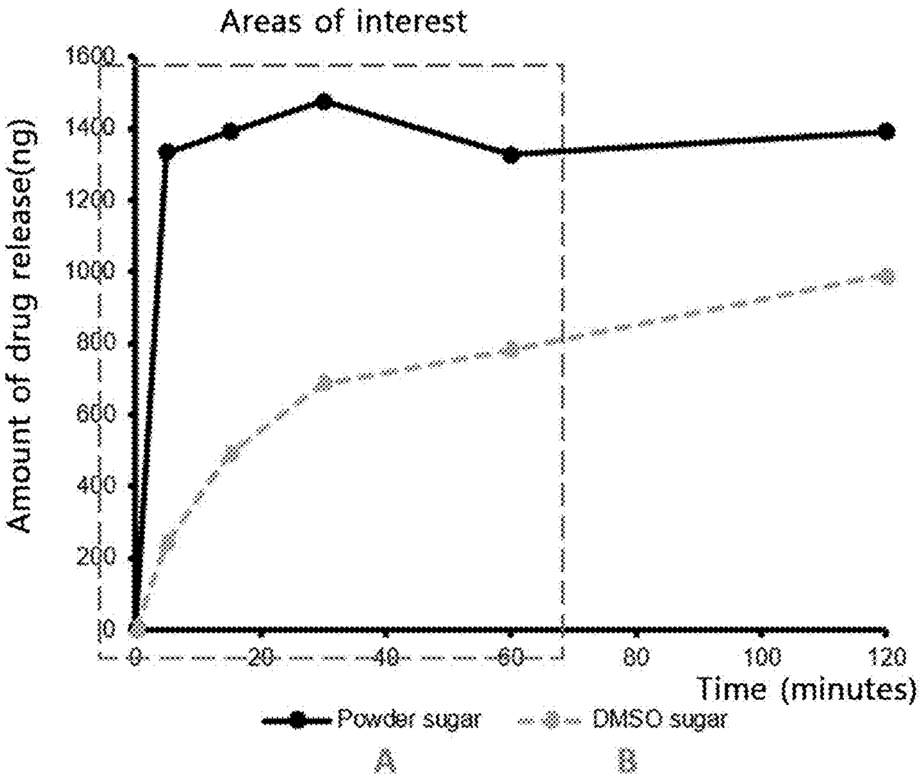

【FIG. 16】
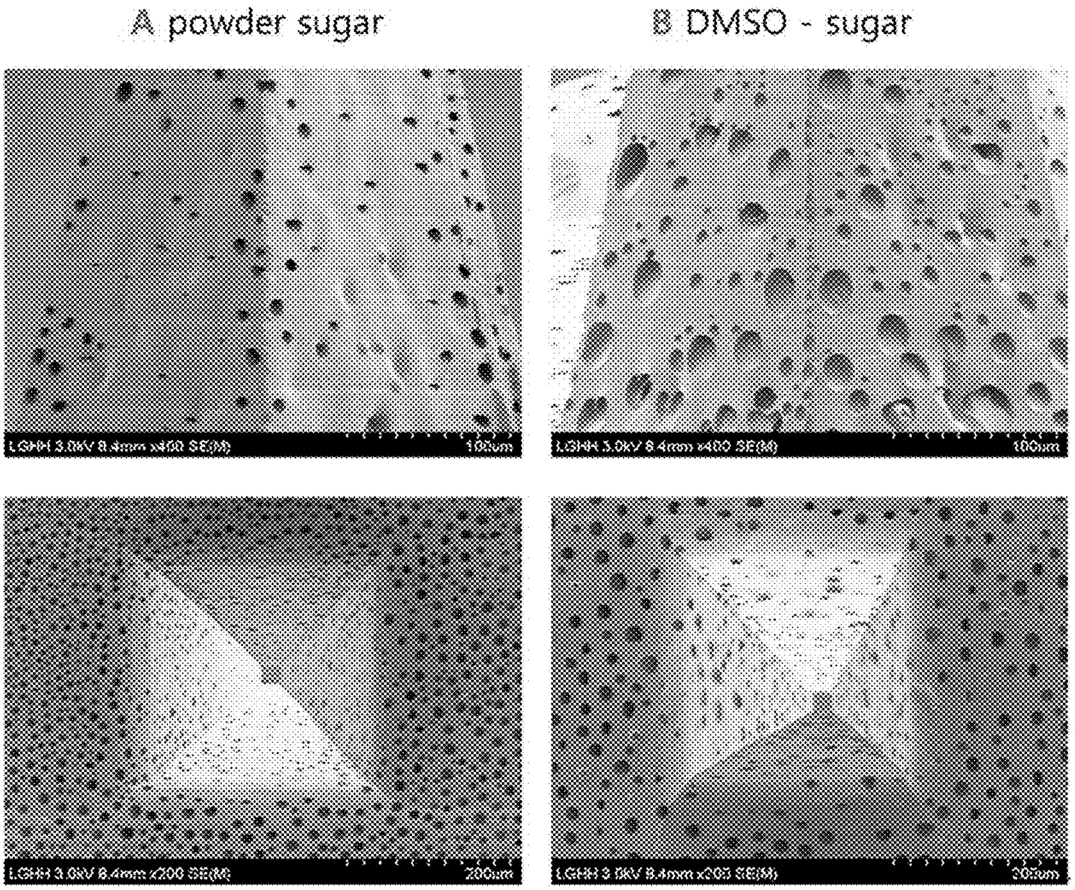
【FIG. 17】
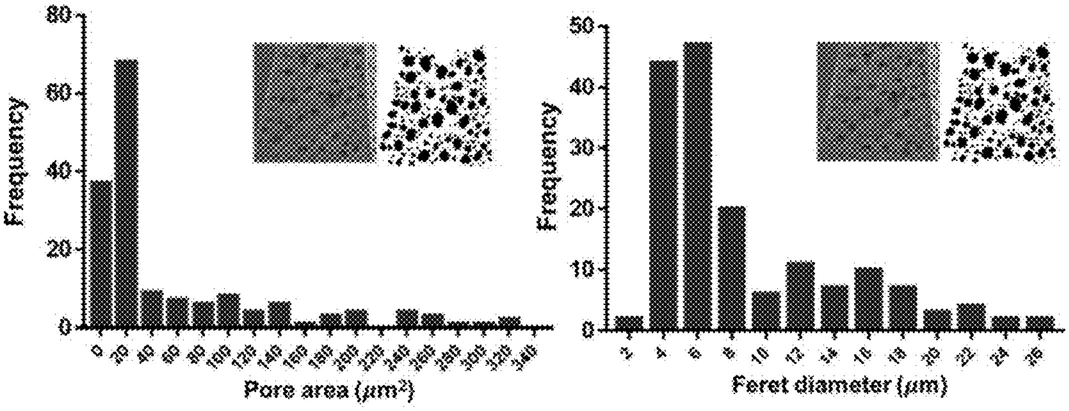

SOLID MICRONEEDLE COMPRISING DRUG AND METHOD FOR MANUFACTURING THE SAME

TECHNICAL FIELD

The present disclosure relates to a solid microneedle prepared using a water-insoluble polymer and a method for manufacturing the same.

More specifically, it relates to a method of manufacturing a solid microneedle by solvent casting, and a solid microneedle manufactured by the method.

BACKGROUND ART

The stratum corneum (10 to 20 μm), the outer layer of the skin is the biggest barrier of transdermal drug delivery system. In the case of the transdermal delivery through diffusion as generally used, it is allowable for only the molecules having a molecular weight of 350 or less or an appropriate ratio of hydrophilic and lipophilic properties (Log P 1.0 to 4). Microneedles with a height of tens to hundreds of micrometers can effectively deliver drugs with minimized destruction of the stratum corneum, minimized pain and increased patient compliance, compared to generally used syringe injections. In addition, in the case of using a microneedle for delivery of a protein-based drug, the drug is not easily degraded, and thus may be efficiently delivered because it does not need the gastrointestinal absorption step unlike oral delivery.

Microneedles are classified into polymer-based water-soluble microneedles, insoluble solid microneedles and hollow-type microneedles with internal microtubes, and each has different characteristics. The solid microneedles generally have advantages over soluble microneedles. They have higher strength and stability and can be repeatedly inserted, but there are technical limitations in processing and molding polymers due to the robust hardness.

PRIOR ART LITERATURE

Patent Literature

WO 2014/15165

Non-Patent Literature

Non-patent literature 1: Silk fibroin microneedle patches for the sustained release of levonorgestrel, Applied biomaterials, 2020

Non-patent literature 2: Rapidly separable microneedle patch for the sustained release of a contraceptive. Nature Biomedical Engineering, 2019

DISCLOSURE

Technical Problem

The technologies described in the prior art literatures require expensive and sophisticated processes such as lithography or hot embossing. In addition, due to lack of stable physical properties or strength and the safety issue of materials and solvents, the technologies are somewhat far from commercialization. In particular, in the case of PLAs (poly lactic acids) approved as GRAS (generally recognized as safe) by the FDA, there are difficulties in the process of molding them into microneedles, and thus the manufacturing process is not sufficiently developed.

In addition, there are problems that the non-patent literature 1 require the complex and sophisticated technologies for separately producing microparticles, and the non-patent literature 2 has the potential risks because a part of the structure is separated and remains into the body.

Therefore, in order to solve the above problems, it has been tried to provide a technology for manufacturing a drug-containing solid microneedle capable of releasing the drug in a rapid or a sustained manner according to the intended purpose, and the present disclosure has been completed by verifying that microneedles can be manufactured by solvent casting a water-insoluble PLA and specific sugars together.

Technical Solution

One aspect of the present disclosure relates to a technology for imparting a drug release function to a solid microneedle, wherein the microneedle is manufactured by solvent casting at a low temperature using the composition comprising water-insoluble polymer(s) and specific organic solvent(s), and wherein the composition also comprises sugar and drug. In the present disclosure, depending on the purpose, a function of rapidly releasing and delivering the drug in a short period of time or a function of slowly releasing the drug (sustained release type) can be selectively provided.

The microneedles (MN) for drug delivery are classified into insoluble and soluble types. Again, the insoluble type microneedles are classified into solid and coated types, and the soluble type microneedles are classified into dissolvable and hollow types.

The solid type microneedle has conventionally been manufactured through a semiconductor process or thermoforming method. However, the devices for these methods are quite expensive and the physical property is determined by the used device, and thus it is difficult to form an MN with various physical properties using these methods. In a solvent casting method, on the other hand, since the physical properties of the formed MN are affected by the injected solution, it is possible to make MNs with various physical properties even by one device.

The present disclosure relates to a method for manufacturing a drug-containing solid type microneedle by solvent casting, characterized by comprising: (a) preparing a polymer solution by dissolving a water-insoluble polymer in a solvent; (b) adding a sugar and a drug to the polymer solution, wherein the sugar is added in powder form; (c) injecting the polymer solution containing the sugar and the drug into a microneedle mold; and (d) drying and separating the microneedle from the mold. Each step is described in more detail below.

(a) The Step of Preparing a Polymer Solution by Dissolving a Water-Insoluble Polymer in a Solvent:

PLA (polylactic acid) may be preferably used as a water-insoluble polymer. Among PLA having various molecular weights and physical properties, D,L-PLA having an inherent viscosity (IV) in the range of 0.25 to 1.7 (inherent viscosity has a dimensionless unit) can be preferably used in terms of microneedle fabrication. The PLA may preferably be dissolved at 5 to 15% by weight in an organic solvent.

As the solvent, acetone, DMF (dimethylformamide), DMSO (dimethylsulfoxide), and the like can be used, and these solvents may not deform the mold (e.g., PDMS mold).

Preferably, DMSO can be used as the solvent. Because DMSO shows excellent solubility for various types of proteins or compounds, and hydrophilic or hydrophobic drugs, it makes hydrophobic drugs can be loaded in microneedle unlike the existing microneedles.

Acetonitrile commonly used in the current polylactic acid (PLA) microneedle fabrication by solvent casting, may remain in microneedle after the fabrication and thus the fabricated microneedle is not allowable in cosmetic field because of the safety issues. In addition, the fabricated microneedle has a poor quality due to bubbles generated during the manufacturing process.

In the case of using DMSO instead of acetonitrile in manufacturing PLA-based MN by solvent casting, i) DMSO is allowable in the cosmetic field, so there is no safety problem even if it remains, and ii) it makes the reduced bubbles during the microneedle fabrication compared to acetontrile, and thus the risk of quality deterioration is also reduced.

The present disclosure provides the conditions for the PLA microneedle fabrication, which can solve the problems that the microneedle structure was not formed due to excessively low viscosity of the preparing solution or excessive bubble generation. Preferably, the content of D,L-PLA having an inherent viscosity (IV) of 0.25-1.7 is 5-15 w % and DMSO is used together.

(b) The Step of Adding Sugar and Drug to the Polymer Solution:

As in the step (a) above, PLA is dissolved in the solvent, and then the sugar and the drug are dissolved. If the order of dissolution is changed in the process, precipitation of PLA may occur. Here, the sugar can be preferably added to 0.5 to 2% by weight of the final concentration in the polymer solution. Some kinds of sugars may cause problems such as precipitation of PLA, but it was found that glucose, sucrose, and trehalose may form stable solutions. If the sugar content is less than 0.5% by weight, pores may not be sufficiently formed and thus the drug may not be easily released. If the sugar content is 2% by weight or more, the PLA and the sugar in the solvent may be precipitated.

The PLA solution has a very high viscosity. So, when sugar is added in the form of powder and dissolved for a short time, the sugar may not be finely dispersed in the polymer solution for preparing the microneedle. Thus, using sugar in the form of power may form thick and large pores structure with the small total specific surface area, resulting in rapid drug release. The prepared microneedle may have larger loading amount of the drug, compared to the tip coating of a solid microneedle. In addition, the microneedle can have increased drug permeation compared to cream formulations, and can show effective skin perforation efficacy due to higher needle stiffness than soluble microneedles.

Preferably, when adding the sugar in a powder form and then stirring for a short time (e.g., for 1 to 10 minutes), the prepared microneedle may form large pores upon applying to the skin while the sugar in the microneedle is dissolved by moisture in the skin, resulting in rapid release. If the microneedle is attached for a long time, it may cause problems that the microneedle is detached with body movement due to the small needle size. Thus, the rapid release of the drug may be advantageous.

The rapid release of the drug as mentioned in the specification means that the drug loaded in the microneedle is released at least 50%, at least 60%, at least 70%, at least 80%, or preferably at least 90% relative to the total content of the drug within 2 hours, within 1 hour and 30 minutes, within 1 hour, within 30 minutes, within 20 minutes, within 10 minutes, or within 5 minutes from the time the microneedle is applied to the skin.

On the other hand, if the sugar previously dissolved in a solvent by heating is added, the sugar is finely dispersed in the solution, resulting in a mesophorous structure with small pore passages inside the microneedle structure (the structure with small pore passages and large specific surface area like the internal structure of charcoal), allowing for slow (sustained) release of the drug. The slow (sustained) release of the drug as mentioned in the specification means that the drug is continuously released for more than 100 hours, more than 150 hours, more than 200 hours, more than 250 hours, or more than 300 hours from the time the microneedle is applied to the skin.

Among various kinds of sugars, trehalose may make the drug be released for more than 12 days, and it is most preferable to select trehalose for a sustained-release microneedle structure. More specifically, it is most preferred that the content of trehalose is 1±0.5% for preparing the microneedle with the sustained-release function.

The drug that can be applied to the microneedle system is not particularly limited to specific types, and may be, for example, cosmetic ingredients, chemical drugs, proteins, peptide drugs, nucleic acid molecules, nanoparticles, anti-wrinkle agents, skin aging inhibitors, skin whitening agents, antioxidants agents, anti-inflammatory agents, analgesics, polyphenols, natural materials, plant extracts, hydrophilic drugs, hydrophobic drugs, etc., but are not limited thereto.

(c) The Step of Injecting the Polymer Solution Containing Sugar and Drug into a Microneedle Mold:

The solution prepared as described above is poured into a mold (e.g., PDMS mold) after degassing. Here, preferably, a vacuum may be applied at the bottom part of the mold to allow sufficient injection of the solution into the microstructure mold. This process can take about 15±5 minutes.

(d) The Step of Drying and Separating the Microneedles from the Mold:

The viscosity and evaporation level of the polymer solution for preparing the microneedle is preferably in an appropriate range. If the viscosity is too low or too high, the microneedle structure may not be formed due to the bubbles generated by rapid evaporation of the solvent during the drying process.

Accordingly, drying may be carried out by putting the filled mold at the low temperature of 40° C. to 60° C. (e.g., in an oven at 50±5° C.) for 6 hours or more. Specifically, when preparing PLA using DMSO as the solvent, it is preferable to volatilize the solvent at a low temperature of about 50±5° C. to prevent bubble generation. A drying time for 6 hours or more is suitable, and it may make about 99% of the solvent be evaporated. Then, the dried microneedle structure may be removed from the mold.

Another aspect of the present disclosure is to provide a solid type microneedle containing PLA (Poly Lactic Acid), sugar and drug, wherein the sugar and the drug are included in the microneedle, and when the microneedle is applied to the skin, the drug may be released while the sugar included in the microneedle is dissolved by moisture in the skin.

The solid microneedle containing the drug may selectively have a function of rapidly releasing and delivering the drug in a short period of time, or a function of slowly releasing the drug (sustained-release type) depending on the manner of adding sugar.

The sugar may be one or more selected from glucose, sucrose and trehalose, and preferably, glucose or sucrose may be used in terms of rapid release.

If the prepared solid microneedle is immersed in distilled water at 37° C., and if being observed after 48 hours, the pores may be formed on the surface of the microneedle. The average diameter of the pores may be 1 to 50 μm, 2 to 25 μm, 5 to 25 μm, 5 to 15 μm, or 5 to 10 μm, and the average area of the pores may be 1 to 200 $\mu m^2$, 5 to 150 $\mu m^2$, 10 to 100 $\mu m^2$, 20 to 80 $\mu m^2$, 30 to 70 $\mu m^2$ or 40 to 60 $\mu m^2$. In addition, the pore ratio (a ratio of pores to the microneedle surface in terms of surface area) may be 5 to 60%, 10 to 50%, 20 to 40%, or 30 to 35%.

As such, the present disclosure provides a new strategy for the manufacture of PLA solid microneedles based on a solvent-casting process. This approach offers extreme simplicity, extensive geometric capabilities, cost-efficiency and scalability based on high-fidelity replicas. In addition, even though the microneedles have various heights (250-500 μm), these microneedles may be efficiently penetrated into the stratum corneum of the skin due to the appropriate mechanical strength. The Microneedles can be also utilized in a variety of ways. For examples, the PLA microneedles may be used together with a sponge-type reservoir and a sheet mask to exhibit synergistic effects for transdermal delivery.

Because the method according to the present disclosure does not use heating to melt water-insoluble polymers unlike the existing PLA processes, the prepared microstructure may have the height of 250 μm to 500 μm through micromolding, and can be widely applied to mask packs, basic products (for improving delivery of active ingredients) and prescription drugs (patches for drug delivery, etc.).

The shape of the microneedle may be any shape such as square pyramid shape, triangular pyramid shape, stepped pyramid shape, microblade shape, bullet shape, etc., and preferably the length (the height of the microneedle) may be in the range of 20 μm to 2 mm, but is not limited thereto.

All ingredients described in the present disclosure do not exceed the maximum use limit stipulated by laws, preferably by the related laws and regulations of Korea, China, the United States, Europe, Japan, etc. (e.g., Regulations on Cosmetics Safety Standards (Korea), Cosmetics Safety Technical Standards (China)). That is, preferably, the cosmetic compositions, cosmetic products, or personal care compositions according to the present disclosure contains the components according to the present disclosure within the content limits permitted by the relevant laws and regulations of each country.

Advantageous Effects

The present disclosure provides a solvent casting composition for preparing a microneedle using a biocompatible water-insoluble polymer and a solvent, and a microneedle manufacturing technology using the same. The present disclosure can also provide the method for inexpensively preparing a solid microneedles with various physicochemical properties (strength, biodegradability, etc.) without high temperature, high pressure or expensive manufacturing techniques during the manufacturing process.

The manufacturing technology of the present disclosure can control the release rate depending on the intended purposes. The prepared microneedle may be a rapid-release type rapidly releasing the drug or a sustained-release type releasing the drug for a long time. The manufacturing technology according to the present disclosure may be used for preparing the microneedle containing various cosmetic or pharmaceutical active ingredients to have the appropriate release properties suitable for the active ingredients.

BRIEF DESCRIPTION OF THE DRAWINGS

FIG. 1 is a schematic diagram showing a manufacturing process of a PLA microneedle structure by solvent casting method according to the present disclosure.

FIG. 2 shows the images of the microneedle arrays prepared in Example I-1 and Comparative Example I-1, and the measured amounts of residual solvent.

FIG. 3 is a graph showing some conditions suitable for microneedle molding among the compositions of Table 1.

FIG. 4 shows scanning electron microscope (SEM) images of the microneedle fabricated in Example I-1.

FIG. 5 shows the result of observing the residue of DMSO solvent during the drying process (left) and the result of examining the PLA microneedles hydrolysis under physiological conditions (right).

FIG. 6 demonstrates force-strain graphs showing the results of measuring the strength of a single microneedle structure by compression test.

FIG. 7 shows the compression test results of the PLA microneedle.

FIGS. 8A and 8B are the result showing the penetration efficiency and the robustness of the structure when the microneedle fabricated in Example I-1 is repeatedly inserted into the human skin.

FIG. 9 shows the difference in biodegradability when the dry weight of PLA is changed in the composition corresponding to the conditions of Example I-1.

Left: shows the result of observing the difference in strength (physical properties) according to the concentration of PLA in the solvent (DMSO). The difference was confirmed in that the strength (or physical properties) of the microneedle can be adjusted in various ways. Existing PLA MN is produced by 1) hot-pressing method or 2) solvent casting method (Corium patent), and it shows unified strength.

Right: The result of observing the difference in biodegradability according to the concentration of PLA in the solvent (DMSO) is shown. The difference was confirmed in that the biodegradability of the biodegradable microneedle can be adjusted.

FIG. 10 shows the results of Franz diffusion cell experiments after applying PLA microneedles combined with the sponge-type reservoir patch or a facial mask sheet.

FIG. 11 is a schematic diagram showing the process for manufacturing a microneedle structure containing sugar and PLA by solvent casting.

FIG. 12 shows scanning electron microscope (SEM) images of microneedles prepared in Comparative Example II-1 and Example II-9.

FIG. 13 shows the release of the model drug (FITC) according to the type and content of sugar.

FIG. 14 is the result showing the skin permeability of the drug when applied to pig skin after manufactured by combining model drugs FITC and retinol under the conditions of Example II-9.

FIG. 15 shows the results of measuring the release amount of the drug (A) when sugar was added in the powder form and (B) in the form of the stock solution sufficiently heated and dissolved in a solvent (DMSO).

FIG. 16 is the result of observing the surface with a scanning electron microscope (SEM) of the prepared microneedles at 48 hours later after immersed in the distilled water of 37° C.: (A) when sugar was added in the powder form and (B) when sugar was added in the form of a stock solution sufficiently heated and dissolved in the solvent (DMSO)

FIG. 17 shows the additional analysis results on the pore characteristics with respect to (A) in FIG. 16.

MODE FOR INVENTION

Hereinafter, the present disclosure will be described in more detail by examples. These examples are intended to illustrate the present disclosure more specifically only, and it will be obvious to those skilled in the art to which the present disclosure pertains that the scope of the present disclosure is not limited by these examples.

Example

I. Preparation of Insoluble Microneedles

Example I-1: the microneedle prepared by dissolving 15% by weight of Resomer® R 207 S PLA in DMSO.

in an appropriate range. If the viscosity was too low or too high, the microneedle structure may not be formed. In addition, the sudden evaporation of the solvent during the drying process may generate air bubbles, making it difficult to form the microneedle structure. Table 1 below shows the formation of the microneedle structure and the strength of the array when prepared by varying the PLA type, the solvent type, and ratio of PLA and the solvent. In the Table 1, the weight of the solvent is the portion excluding the weight of PLA; a, b, and c marks in the blanks means that microneedle structure was not formed.

The strength of the microneedle was measured using a texture analyzer (TA.XTplusC, Stable Micro System, UK). After attaching the microneedle array to the lower part of the sensor, measurement was carried out by moving the press sensor vertically at a speed of 0.1 mm/sec with a trigger force of 10 G. The force measured at a strain of 200 μm was defined as the mechanical strength and used for analysis

TABLE 1

| | | Solvent type PLA concentration | | | | | | | | |
|---|---|---|---|---|---|---|---|---|---|---|
| | | DMSO | | | OMF | | | Acetone | | |
| | | 10% | 15% | 20% | 10% | 15% | 20% | 10% | 15% | 20% |
| PLA molecular weight | 203S | _[a] | _[a] | 221 | _[a] | _[a] | 352 | _[c] | _[c] | _[c] |
| | 205S | _[a] | 461 | 86.66 | _[a] | 884.3 | 309 | _[c] | _[c] | _[c] |
| | 207S | 325 | 774.3 | _[b] | _[a] | 789.6 | _[b] | _[c] | _[c] | _[c] |

[a]Too low viscosity
[b]Too high viscosity
[c]non-uniform drying
Difference in physical properties/strength according to solvent (3 types) and PLA molecular weight/concentration
Optimal condition: PLA 207S 15% in DMSO Comparative Example I-1: the microneedle prepared by dissolving 15% by weight of Resomer® R 207 S PLA in acetonitrile.

Comparative Example I-2: the soluble microneedle prepared by an aqueous solution of hyaluronic acid (the dry weight 10%).

Experimental Example I-1. Manufacturing of PLA Microneedle by Solvent Casting Solutions were prepared by dissolving 5 to 20% by weight of D,L-PLA Resomer® R having different molecular weights (203S, 205S, 207S) from Evonik in various organic solvents. PLA was dissolved in the organic solvent using a stirrer for about 1 hour at room temperature (25° C.). At that time, the insoluble PLA is preferably dissolved at 50% relative humidity (RH) because it absorbs moisture in the air and tends to be precipitated. In the case of the dissolving temperature, the low temperature (<4° C.) may cause precipitation or long dissolution time due to decrease in the solubility of PLA, and the high temperature may cause the reduced moldablity due to evaporation or viscosity reduction of the solvent. Stirring speed depends on the type of the used stirring bar, but around 300 rpm is suitable.

The prepared solutions were applied to a silicon molds, vacuumed for 15 minutes, and dried at 50° C. for more than 6 hours. The dried microneedle structures were separated from the molds (see FIG. 1).

In the micromolding method as shown in FIG. 1, the viscosity and evaporation level of the solution is preferably Example I-1 is the microneedle that 15% by weight of Resomer® R 207S PLA was dissolved in DMSO according to the above optimal condition, Comparative Example I-1 is the microneedle that 15% by weight of Resomer® R 207 S PLA was dissolved in acetonitrile as a solvent commonly used in the previous literatures (KR2015/0130391A, etc.). The microneedle arrays using Example I-1 and Comparative Example I-1 were manufactured and the results are shown in FIG. 2.

As a result of the experiment, it was found that the microneedle structure was not formed due to excessive bubbles when acetonitrile was used as the solvent (FIG. 2).

Meanwhile, FIG. 3 shows the strength of the microneedle structures that were able to form the structures among the conditions shown in Table 1.

FIG. 4 shows the manufactured microneedles having various heights according to Example I-1 of the present disclosure, as observed with a scanning electron microscope (SEM). The diameters of the needle tip were 10 to 20 km.

Residual Solvent during the drying process was observed. When the amount of residual solvent was measured during drying, the residual amount of DMSO was slightly smaller. Considering the toxicity to the human body, acetonitrile requires complete removal, but DMSO as a biologically safe solvent does not need the complete removal because it has been used in the formulation of various drugs. Therefore, DMSO is more suitable for biosafety and manufacturing process than acetonitrile. The residual solvent was calculated using the theoretical mass of DMSO and PLA and the reduced weight according to the drying time [mass (by time)−mass (initial, 0 min)/theoretical mass of DMSO as added].

In addition, residual DMSO during the drying process was observed (see the left drawing of FIG. 5). After 330 minutes, ~98% of DMSO had evaporated. This result means that there is no toxicity by the residual DMSO in the PLA microneedles. Because only a portion of the microneedle tips is penetrated into the skin, the amount of residual DMSO delivered to the punctured skin may be negligible.

PLA is a widely used material for 3D scaffolds in the tissue engineering and implantable devices because of its biocompatibility and biodegradability. Degradability and hydrolysis of the PLA microneedle under almost physiological conditions were investigated (see the right drawing of FIG. 5). Degradation of PLA has been studied under various conditions. Proteinase K is known to effectively catalyze the degradation of PLA in previous studies and has been used for biodegradability evaluation. Interestingly, it was found that higher mass ratio of PLA results in higher degradation rate of the PLA microneedle. After 23 days of culture, the microneedles prepared by 5%, 10%, and 15% of casting solutions showed residual weight ratios of 91.39%, 82.72%, and 86.39%, respectively. Previous studies have shown that the concentration of PLA in a solution containing an organic solvent for preparing films or scaffolding affects the porosity and pore size of cavities in PLA-based structures. It has been observed that the porosity and pore size may affect the hydrolysis and degradation of PLA. The difference in biodegradability according to the concentration of PLA seems to be due to the difference in pore size or porosity of the structure. After placing the microneedle structure in PBS containing proteinase K at 37° C., the degree of biodegradation was observed by measuring the dry mass at each time point. Proteinase K is known to hydrolyze PLA and has been used to measure biodegradability in the literature. (Li, F.; Wang, S.; Liu, W.; Chen, G. Purification and characterization of poly (L-lactic acid)-degrading enzymes from Amycolatopsis *orientalis* ssp. *orientalis*. FEMS microbiology letters 2008, 282, 52-58; Huang, Q.; Hiyama, M.; Kabe, T.; Kimura, S.; Iwata, T. Enzymatic self-biodegradation of poly (1-lactic acid) films by embedded heat-treated and immobilized proteinase K. Biomacromolecules 2020, 21, 3301-3307.)

Experimental Example I-2. Measurement of Strength of Microneedle Single Structure To analyze the physical properties of the microneedle, the strength of the microneedle array was measured (FIG. 6). Example I-1 (a microneedle manufactured by using the solution containing 15% by weight of 207S-PLA dissolved in DMSO) and Comparative Example I-2 (hyaluronic acid-based soluble microneedle having 10% of dry weight) were analyzed for the mechanical properties. The strength of the microneedles was measured using a texture analyzer (TA.XTplusC, Stable Micro System, UK). After attaching the microneedle array to the lower part of the sensor, the measurement was carried out by moving the pressing sensor vertically at a speed of 1.2 mm/sec with a trigger force of 0.003 N. The force (stress) against the displacement (strain) was measured.

Compared to the force-displacement curve of the PLA microneedle, penetration failure was observed in the dissolving microneedle. In the case of the hyaluronic acid-soluble microneedle, there was the irreversible failure of the array structure in the increased strain according to the force-strain graph (FIG. 6(*b*)). On the other hand, in the case of the PLA microneedle, there was no failure (FIG. 6(*a*)). Because the minimum force required for a single array structure of the microneedle to penetrate the skin is 0.058 N, the PLA microneedle ensures the sufficient mechanical strength to penetrate human skin.

In addition, in the texture analysis of the microneedle arrays, there was no significant difference between the microneedles having the height of 250, 300, or 350 m (FIG. 7 upper drawing).

In the compression test of a single array of the PLA microneedle, when it was subjected to 0.1 N, the tip of the microneedle structure (about 5% of the total height) was slightly bent, but there was no significant deformation of the entire structure (FIG. 7 bottom left drawing). This observation is similar to the compression test of the microneedle with the compression force of 5 N (0.06 N per a single array) (FIG. 7 bottom right drawing). This means the PLA microneedles show no significant deformation at 0.058 N as required to penetrate the skin.

Experimental Example I-3. Evaluation of Repeated Insertion of the Microneedle

It is known that solid microneedles can be repeatedly inserted several times because they are generally stronger than soluble microneedles. The Experimental Example I-2 also showed the stronger physical strength. It was evaluated whether the PLA microneedle of the present disclosure can be repeatedly applied to the actual skin several times.

As shown in FIG. 8*a*, it was found that the penetration efficiency was maintained at 90% or more even when inserted into the actual human skin eight or more times. In addition, when observed under a microscope whether or not the structure of the microneedle was changed after every insertion, the change in the structure was not observed (FIG. 8*b*). After insertion to human skin, application for 10 seconds and removal, 12.5% *gardenia* blue pigment was applied to the applied site for 15 minutes for evaluating penetration efficiency. Thereafter, after removing the pigment in flowing water, it was observed through an optical microscope. The penetration efficiency can be evaluated by observing the strong dying level in the pores of the penetrated stratum corneum.

Experimental Example I-4. Difference in Biodegradability by PLA Content in the Microneedle Manufacturing PLA is a biocompatible and biodegradable polymer that can be degraded in the body, so it is used as an implant or tissue scaffold. In the manufacturing method according to the present disclosure, the microneedles can be manufactured by varying the content of PLA in the solvent unlike the conventional heat compression methods. The microneedles made of solutions having different contents of PLA were immersed in PBS containing proteinase K at 37° C. and biodegradability were observed.

As shown in FIG. 9, the biodegradability was somewhat faster when the content of PLA in the solution was increased, and this difference was evident around the 10th day. This means that a microneedle having superior biodegradability can be prepared by the manufacturing method of the present disclosure.

Experimental Example I-5. Verification of Linkage Possibility with Various Platforms (a) First, a PLA microneedle patch combined with a sponge-type reservoir was applied, followed by a Franz diffusion cell experiment. Specifically, after attaching the combined patch to the pig skin assembled in the Franz-cell, a FITC solution (50,000 ng/ml) was injected into the PU sponge included in the patch. After 16 hours, the pig skin and Franz-cell Reservoir solution were analyzed. As a result of using microneedles with height of 250, 350 or 500 μm, the transdermal delivery of FITC is facilitated through the micropores in the skin formed by the application of the microneedle (FIG. 10, left drawing). The application of 250 μm PLA microneedles combined with the PU foam showed a 3.3-fold increase in transdermal delivery of FITC. Compared to the negative control (topical application of FITC solution to the pig skin), the amount of FITC delivered to the dermis and Franz cell reservoir (Receptor Chamber) was dramatically increased. This means that the micropores and channels formed in the skin can facilitate the efficient delivery of a drug molecule. According to previous studies, the stratum corneum (SC) of the pig skin is 20-26 μm thick and the epidermis is 30-140 μm thick. Both of 350 and 500 km PLA microneedles improved the transdermal delivery of FITC (5.6-fold and 6.6-fold, respectively). No significant difference was observed in the delivery efficiency of the 350 and 500 μm microneedles. This observation implies that longer length of microneedles may not always result in higher transdermal delivery efficiencies.

(b) The role of vitamin C in the skin is receiving attention. It is known that Vitamin C i) is involved in the formation of collagen by acting as a cofactor for proline and lysine hydroxylase, ii) is a powerful antioxidant as a free radical scavenger, and iii) inhibits melanin production and is involved in differentiation or proliferation of skin constituent cells such as keratinocytes and fibroblasts. Evidences for the other various roles of vitamin C in UV-induced intrinsic and extrinsic skin aging are still emerging. For these reasons, the topical application of vitamin C in cosmetic formulations has been suggested as an effective approach to skin protection against endogenous or UV-induced photo-aging. However, transdermal delivery of vitamin C suffers from numerous factors.

In this experimental example, vitamin C was delivered using a sheet mask soaked in a 25% solution. PLA microneedles with a length of 250 km were applied to the pig skin. After removing the microneedle, the mask sheet soaked in a 25% vitamin C solution was applied to the needle treatment area. After 3 hours, the vitamin C contents in the skin substructures and Franz cell reservoir were analyzed. Data are presented by calculating the mean of n=3 replicates and standard deviation bars are indicated (*significantly different: Student's t-test, $p<0.05$).

Experimental results have shown that skin occlusion (by covering the skin with tape, sheet or other impermeable dressing material) can increase transdermal delivery efficiency by increasing stratum corneum hydration and by altering the intracellular lipid organization. Some studies suggest that the increased skin surface temperature and blood flow by the skin occlusion may also affect transdermal delivery efficiency. A sheet mask, also called a 'facial mask' or 'mask pack', is widely used as one of the important categories of cosmetics, and provides the skin occlusive effect. As in previous studies on the occlusive effects in transdermal delivery, the application of the sheet mask increased vitamin C delivery to the skin by 1.9-fold compared to application of the topical solution. A dramatic increase (3-fold) of vitamin C in the dermis was observed. Interestingly, the application of the sheet mask and the PLA microneedle together (specifically, application of the sheet mask to the pig skin pre-treated with the microneedle) dramatically increased the transdermal delivery of vitamin C: increase by 12.9-fold and 6.8-fold respectively, compared to the negative control group (topical solution application) and the sheet mask alone group (see FIG. 10 right drawing). It is noteworthy that in the amount of vitamin C delivered to the epidermis, there is no significant difference between the three groups as if saturated. Similar result was observed in the sponge patch experiment. The previous studies through the Franz diffusion cell experiments have shown that the amount of drug (or target molecule) tends to saturate in the skin tissue, and some simulation studies have shown that the drug concentration in the epidermis reaches a plateau within about 3 hours.

II. Preparation of Insoluble Microneedles for Drug Release

Comparative Example II-1: the microneedle manufactured by dissolving 15% by weight of Resomer® R 207 S PLA in DMSO.

Examples II-1, II-2, II-3, II-4: the microneedles manufactured by dissolving 15% by weight of Resomer® R 207 S PLA in DMSO, and then dissolving 0.25, 0.5, 1, and 2% by weight of glucose, respectively.

Examples II-5, II-6, II-7, II-8: the microneedles manufactured by dissolving 15% by weight of Resomer® R 207 S PLA in DMSO, and then dissolving 0.25, 0.5, 1, and 2% by weight of sucrose, respectively.

Comparative Examples II-2, II-3, II-4, II-5: the microneedles manufactured by dissolving 15% by weight of Resomer® R 207 S PLA in DMSO, and then dissolving 0.25, 0.5, 1, and 2% by weight of lactose, respectively.

Examples II-9, II-10, II-11, II-12: the microneedles manufactured by dissolving 15% by weight of Resomer® R 207 S PLA in DMSO, and then dissolving 0.25, 0.5, 1, and 2% by weight of trehalose, respectively.

Experimental Example II-1. Manufacture of Insoluble Microneedle Structure for Sustained Drug Release The insoluble microneedles for the drug release were manufactured by the solvent casting method of Example 1, and an additional process was carried out. PLA was dissolved in the organic solvent using a stirrer for about 1 hour at room temperature (25° C.). Because some kinds of solvents have a characteristic of absorbing moisture in the air, they can cause precipitation of water-insoluble PLA. Therefore, PLA is preferably dissolved at 50% relative humidity (RH). Firstly, PLA was dissolved in the solvent, and the sugar was added little by little (0.2% input/1 min) while stirring at 50% or less of relative humidity (RH). Rapid addition of the sugar caused irreversible precipitation of PLA and sugar.

It is tested whether the addition of sugar in the manufacturing of the PLA microneedle allows for a sustained release of the drug. During the process of manufacturing the PLA microneedle by the same solvent casting method as in Example I-1 described above, the solvent and PLA were firstly dissolved, and then the sugar and the drug were dissolved under the controlled relative humidity (FIG. 11). When inserted into the body, the sugar molecules can be dissolved by moisture in the body, and porous structures can be formed, and the loaded drug can be released to the outside of the structure through the expanded surface area formed by the dissolution of the sugar.

The types of sugars that can be mixed during the manufacturing process may be limited, but it was found that the formation of the microneedle can differ depending on the type of sugar. In the case of lactose, it caused precipitation of PLA, so it was not suitable. It was found that the degree of the sustained release can differ depending on the type and content of the sugar included (Table 2).

TABLE 2

| | PLA % | sugar type | | Whether micro-needle is formed | Whether the drug is released in a sustained manner after 24 hours |
|---|---|---|---|---|---|
| Comparative Example II-1 | 15 | | | O | X |
| Example II-1 | 15 | Glucose | 0.25% | O | X |
| Example II-2 | 15 | Glucose | 0.50% | O | X |
| Example II-3 | 15 | Glucose | 1% | O | Δ |
| Example II-4 | 15 | Glucose | 2% | O | X |
| Example II-5 | 15 | Sucrose | 0.25% | O | X |
| Example II-6 | 15 | Sucrose | 0.50% | O | X |
| Example II-7 | 15 | Sucrose | 1% | O | Δ |
| Example II-8 | 15 | Sucrose | 2% | O | X |
| Comparative Example II-2 | 15 | Lactose | 0.25% | X | X |
| Comparative Example II-3 | 15 | Lactose | 0.50% | X | X |
| Comparative Example II-4 | 15 | Lactose | 1% | X | X |
| Comparative Example II-5 | 15 | Lactose | 2% | X | X |
| Example II-9 | 15 | Trehalose | 0.25% | O | X |
| Example II-10 | 15 | Trehalose | 0.50% | O | O |
| Example II-11 | 15 | Trehalose | 1% | O | O |
| Example II-12 | 15 | Trehalose | 2% | O | X |

When immersing the microneedles of Comparative Example II-1 and Example II-9 in distilled water at 37° C., the surface images with a scanning electron microscope (SEM) after 48 hours were shown in FIG. 12. In the case of Example II-9 having the addition of 0.25% trehalose, a porous structure was formed on the surface of the PLA by the dissolution of trehalose.

In addition, in order to evaluate the drug release pattern according to the type and concentration of sugar, after immersing in distilled water at 37° C., the released amount of the drug was measured by analyzing the fluorescence of FITC, and the results are shown in FIG. 13. This is the cumulative released amount, and as a result of the experiment, it was found that the release pattern of the drug was different depending on the type concentration of sugar (FIG. 13).

In general, when the sugar content was high, the large and rapid release was observed. In addition, when the sugar content was low, the small and slow release was observed. In the case of Examples II-1, II-2, II-3 and II-4 having the addition of glucose and Examples II-5, II-6, II-7 and II-8 having the addition of sucrose, most of the drugs were rapidly released. However, in the case of trehalose, the drug was released slowly under the condition of 0.5% to 1%, and the drug release was observed until about 300 hours.

In FIG. 14, a microneedle structure with a height of 500 μm was prepared by adding 1% trehalose, 1% FITC (model drug) and 1% of retinol. Then, the insertion/application time to the pig skin was changed to 1 hour and 4 hours, and the amount permeated to the skin was analyzed (Franz cell experiment). After 1 hour of application, it was found that the model drugs were delivered to the dermis and epidermis, and after 4 hours of application, it was found that more drugs was migrated to the dermis. Accordingly, it was confirmed that a high content of oil-soluble retinol could be loaded and delivered using the organic solvent DMSO. This means that the oil-soluble drugs can be loaded in higher content, compared to the existing water-soluble microneedles.

Experimental Example II-2. Manufacture of Insoluble Microneedle Structure for Fast Drug Release In manufacturing the PLA microneedle, we tested whether the addition of sugar can make rapid release of the drug. During the process of manufacturing the PLA microneedle by the same solvent casting method as in Example I-1 described above, trehalose and FITC (a model drug) were dissolved. Specifically, PLA (15 w %) was firstly dissolved in DMSO, and then trehalose was added in the powder form to the final concentration of 1% by weight, followed by stirring for a short time of about 7 minutes, and then casting was carried out (A).

In the comparative example, a stock solution dissolving 10% of trehalose in DMSO by heating was used. Specifically, PLA (15 w %) was firstly dissolved in DMSO, and then the stock solution was added to the final concentration of 1% by weight, followed by sufficient stirring, and then casting was carried out (B).

In order to evaluate the drug release pattern for A and B prepared above, after immersing in distilled water at 37° C., the released amount of the drug was measured by analyzing the fluorescence of FITC, and the results are shown in FIG. 15. The fluorescence of FITC was measured using a photoluminescence spectrometer.

As a result of the experiment, in the case of A, it was found that all of the drug could be released within 1 to 2 hours. Not limited to theory, it is believed that because the PLA solution has a very high viscosity, the sugar added in the form of powder is not sufficiently finely dispersed in the needle solution, so the formed pores are thick and large, and the formed pore structure has small total specific surface area, resulting in rapid release of the drug. The solvent casting method by the addition of the sugar in the form of powder has the following advantages: a larger loading amount of drug than coating the tip of a solid microneedle, the increased amount of drug permeation compared to cream formulations, and effective skin puncture by higher needle rigidity compared to a soluble microneedle.

On the other hand, in the case of B, it was observed that the drug was released in a sustained manner. This is because the sugar is completely dissolved and is sufficiently finely dispersed in the solution, thus the formed microneedle can make a mesophorous structure upon the application (small pore passage and large total pore specific surface area), resulting in the sustained release of drug.

After immersing A and B prepared by the manufacturing method described above in distilled water at 37° C., the images of the surfaces observed with a scanning electron microscope (SEM) after 48 hours are shown in FIG. 16. In the case of A, the addition of the sugar in the form of powder formed thick and large pores on the surface. In the case of B, the addition of the sugar in the form of fine dispersion prepared by the stock solution formed a mesophorous structure with small pore passages on the surface (FIG. 16).

In addition, the further analysis on the pore characteristics of the solid microneedle A showed that the average diameter of the pores was 8.68 μm, and the average area of the pores was 53.35 $\mu m^2$, in addition, the pore ratio (the ratio of the total pore area to the area of the needle surface) was 33.9%, when the prepared solid microneedle was immersing in distilled water at 37° C. and observed after 48 hours (FIG. 17).

The invention claimed is:

1. A method for manufacturing a solid type microneedle comprising a water-insoluble polymer, sugar and drug by solvent casting, comprising:

(a) preparing a polymer solution by dissolving the water-insoluble polymer in a solvent;

(b) adding the sugar and the drug to the polymer solution, wherein the sugar is added in a powder form and stirring for 1 to 10 minutes to maintain the sugar in an undissolved, dispersed state in the polymer solution;

(c) injecting the polymer solution containing the sugar and the drug into a microneedle mold; and (d) drying and separating the microneedle from the microneedle mold.

2. The method according to claim 1, wherein the sugar included in the microneedle is dissolved by moisture in the skin when the microneedle is applied to the skin and the drug is rapidly released.

3. The method according to claim 1, wherein the water-insoluble polymer is poly lactic acid (PLA).

4. The method according to claim 3, wherein the PLA has an inherent viscosity (IV) of 0.25 to 1.7, and PLA in step (b) is added to have a final concentration of 5 to 15% by weight relative to the total weight of the polymer solution.

5. The method according to claim 1, wherein the sugar in step (b) is added to have a final concentration of 0.5 to 2% by weight relative to the total weight of the polymer solution.

6. The method according to claim 1, wherein the solvent is one or more selected from the group consisting of dimethyl sulfoxide (DMSO), acetone, and dimethylformamide (DMF).

7. The method according to claim 1, wherein the solvent is dimethyl sulfoxide (DMSO).

8. The method according to claim 1, wherein the drying is carried out by evaporating the solvent at a temperature of 40° C. to 60° C.

9. The method according to claim 1, wherein the sugar comprises one or more selected from glucose, sucrose and trehalose.

10. The method according to claim 1, wherein the sugar comprises glucose or sucrose.

11. The method according to claim 1, wherein the solid type microneedle form pores with an average diameter of 1 to 50 μm on the surface of the microneedle when the solid type microneedle is immersed in distilled water at 37° C. and observed after 48 hours.

* * * * *